(12) United States Patent
IDrees

(10) Patent No.: US 9,636,066 B2
(45) Date of Patent: May 2, 2017

(54) HEADBAND MONITORING SYSTEM

(71) Applicant: Umm Al-Qura University, Makkah (SA)

(72) Inventor: Yousef Marouf IDrees, Makkah (SA)

(73) Assignee: Umm Al-Qura University, Makkah (SA)

( * ) Notice: Subject to any disclaimer, the term of this patent is extended or adjusted under 35 U.S.C. 154(b) by 0 days.

(21) Appl. No.: 14/718,455

(22) Filed: May 21, 2015

(65) Prior Publication Data

US 2016/0338636 A1 Nov. 24, 2016

(51) Int. Cl.
*A61B 5/02* (2006.01)
*A61B 5/00* (2006.01)
*A63B 24/00* (2006.01)
*A61B 5/024* (2006.01)
*A41D 20/00* (2006.01)
*A41D 1/00* (2006.01)

(52) U.S. Cl.
CPC ............ *A61B 5/486* (2013.01); *A61B 5/0022* (2013.01); *A61B 5/02438* (2013.01); *A61B 5/6803* (2013.01); *A61B 5/742* (2013.01); *A61B 5/746* (2013.01); *A61B 5/7455* (2013.01); *A63B 24/0062* (2013.01); *A41D 1/002* (2013.01); *A41D 20/00* (2013.01); *A63B 2024/0068* (2013.01)

(58) Field of Classification Search
CPC ........ A41D 1/002; A41D 20/00; A61B 5/486; A61B 5/0022; A61B 5/02438; A61B 5/6803; A61B 5/742; A61B 5/7455; A61B 5/746; A63B 24/0062; A63B 2024/0068
See application file for complete search history.

(56) References Cited

U.S. PATENT DOCUMENTS

| | | | |
|---|---|---|---|
| 5,617,477 | A | 4/1997 | Boyden |
| 5,953,434 | A | 9/1999 | Boyden |
| 6,794,989 | B2 | 9/2004 | Naegely et al. |
| 7,394,912 | B2 | 7/2008 | Whipple |
| 8,043,173 | B2 | 10/2011 | Menalagha et al. |
| 8,804,992 | B2 | 8/2014 | Bailey |
| 2013/0072765 | A1* | 3/2013 | Kahn ........................ A61B 5/01 600/301 |

(Continued)

*Primary Examiner* — Mallika D Fairchild
(74) *Attorney, Agent, or Firm* — Hauptman Ham, LLP

(57) ABSTRACT

A headband monitoring system comprises or consists of an elastic fabric headband for fitting around an individual's head over the individual's forehead, ears and lower back portion of the head. In addition, a pedometer, a heart rate monitor and a number of sensors for detecting number of steps taken and heartbeats in given periods of time and a mini-computer having an input mechanism, data storage, central processing unit and a clock/timer for calculating distance traveled in a given period. Finally, the system includes an individual's smartphone separately disposed from the headband and a Bluetooth transmitter disposed in the elastic fabric band and wirelessly connected to the smartphone for displaying heart rate, steps taken and distance traveled on the smartphone. Finally, a timer and vibrating alarm is disposed in said fabric band for warning an individual that their heart rate has exceeded a predetermined level and that it is time to reduce the exertion over a limited period of time before stopping the exercise.

1 Claim, 3 Drawing Sheets

(56) References Cited

U.S. PATENT DOCUMENTS

2013/0109997 A1* 5/2013 Linke .................. G06F 19/3418
  600/549
2014/0296669 A1* 10/2014 Gertsch ................ A61B 5/6803
  600/324

* cited by examiner

HEADBAND MONITORING SYSTEM

FIELD OF THE INVENTION

This invention relates to a headband monitoring system and more particularly to a fabric headband that monitors heart rate versus exercise and has a sleep mode.

BACKGROUND OF THE INVENTION

Personal wearable communication and entertainment systems are well known and have been in use for over 25 years. For example, Whipple U.S. Pat. No. 7,394,912 discloses an Audio Headband Device. As disclosed, an elastic headband device with integrated audio system includes a stretchable cloth member sized and shaped for positioning about the head and ears of an individual wearer. The cloth member includes a central cavity throughout with first and second side portions and a rear portion. A pair of audio speaker elements are removably disposed within the central cavity of the cloth member at the first and second side portions thereof. A mechanism is also provided for adjusting the relative position of each audio speaker element within the central cavity at its respective side portion to position each element opposite an ear opening of an individual wearer. A central aperture is positioned at the cloth member rear portion for accessing the central cavity. Finally, a plurality of speaker wires are attached to the audio speaker elements within the cloth member central cavity and exit through the central aperture at the rear portion for connection to an audio generation system.

A more recent Menalagha et al. U.S. Pat. No. 8,043,173 discloses a Sports Training System. The patent discloses a training system used in sports or other training that where a participant wears a device with a visual indicator such as a device emitting colored light and an optional signaling device like a vibrator or beeper. The device can be worn on the head, elbow, wrist, waist, knee, ankle or foot or be part of a participant's attire. The device can optionally be embedded in or on a shoe. A motion or position sensor can cause the visual indicator to change color or indication when the wearer is not moving correctly. Also, in some embodiments, a vibration signal can be commanded by a coach or instructor to show that the player is not properly moving. An embedded processor can optionally set up various rhythm patterns used in practice. The device, wherever it is worn or disposed, can optionally be controlled remotely by a coach or instructor using a wireless transmission such as digital or analog radio or light to establish certain rhythms or to signal certain participants. The coach can send different signals to different devices worn by different participants. In a particular shoe embodiment, each of a pair of shoes can optionally communicate with the other member of the pair wirelessly so that a processor in one of the shoes can coordinate a rhythm pattern of vibration or beeping signals between the shoes.

Finally, a U.S. Pat. No. 8,804,992 of Bailey discloses a One-Piece Headband for a Bluetooth Headset. As disclosed, a headset with electronic communications devices such as a cellular telephone and which includes a unitary, one-piece headband that includes a hair comb. The one-piece headband also includes a volume control and an on/off switch and an aerial wire intertwined with the teeth of the comb. Earbuds are also attached to the one-piece headband to be integral unitary therewith.

Notwithstanding the above, it is presently believed that there is a need and a potential commercial market for a headband monitoring system in accordance with the present invention. There should be a commercial market for such systems because they keep track of an exercise such as walking or running versus heart rate and sound an alarm if the heart rate approaches a dangerous level and warns the user to slow their pace.

SUMMARY OF THE INVENTION

A headband monitoring system in accordance with the present invention comprises or consists of:

An elastic fabric band for snuggly fitting around an individual's head over the individual's forehead, ears and lower back portion of the individual's head.

In addition, a pedometer, a heart rate monitor and a number of sensors for detecting the number of steps taken and heartbeats in given periods of time and a mini-computer having an input mechanism, data storage, central processing unit, a clock timer for calculating distance traveled in a given period and an alarm.

Further, an individual's smartphone separate from the elastic fabric band as well as a Bluetooth transmitter disposed in the elastic fabric band are wirelessly connected to the smartphone for displaying heart rate, steps taken and distance traveled on the smartphone. Finally, a clock timer and vibrating alarm are disposed in the fabric band for warning an individual that their heart rate has exceeded a predetermined level and/or that it is time to wake up.

A headband monitoring system according to the preferred embodiment of the invention includes the elements listed above as well as a pair of earphones in the elastic fabric band and a means for music and news deliverable to the earphones from the smartphone.

In addition, the headband monitoring system includes a switch for disconnecting the smartphone from the headband such as an automatic switch for doing so when the headband is turned inside out.

Still further, the system in accordance with the preferred embodiment of the invention includes a sleep mode when the headband is reversed on an individual's head for relative silence.

Finally, the headband system also includes a vibrating alarm indicator connected to the heart rate monitor and activated when the heart rate exceeds a preselected level.

The invention will now be described in connection with the following drawings.

DESCRIPTION OF THE PREFERRED EMBODIMENT OF THE INVENTION

Figure 1:
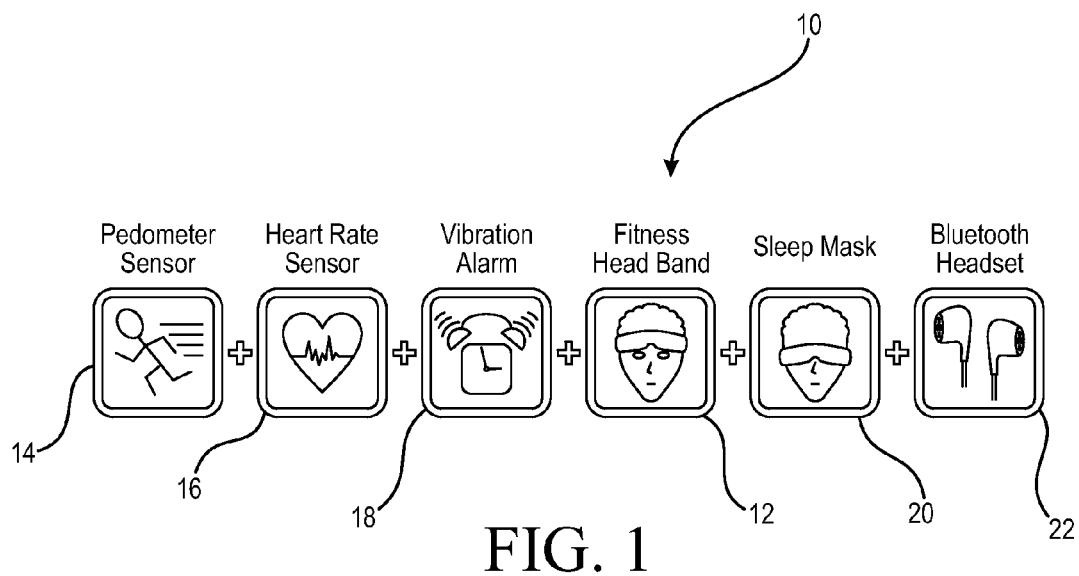
FIG. 1 is a schematic illustration showing the functions of the invention.

As shown in FIG. 1 a headband monitoring system 10 in accordance with a first embodiment of the invention includes a fabric headband 12 that is somewhat elastic due to the stretchable nature of the fabric. The headband 12 has a generally circular shape and is designed to encircle an individual's head. For example, the headband 12 passes around an individual's forehead, ears and lower back portion of the head. The system 10 also includes a pedometer/sensor 14 and a heart rate monitor/sensor 16.

The pedometer/sensor 14 and heart rate monitor/sensor 16 each may be a single unit or multiple units. For example, the pedometer/sensor 14 may include a separate pedometer counter and separate sensor disposed on the waist or ankle with a counter portion connected by wire to the headband 12. Similarly, the heart rate monitor/sensor 16 may be disposed in the headband and connected by wire to a sensor over the heart or pulse of an individual.

In a preferred embodiment of the invention, a clock timer 18 is also disposed in the headband and is integral with or separately disposed in the headband and operatively connected to a vibrator/alarm in the headband. In the preferred embodiment of the invention, the vibrator/alarm is activated when the individual's heart rate approaches a dangerous level. Under such circumstances the vibrator and a text message on the individual's smartphone advise the individual to slow their pace and ease off of the treadmill or pace.

In a preferred embodiment of the invention the fitness headband also includes a sleep mode and serves as a sleep mask 20 and a vibration alarm can be programmed to awake the individual at a given time. For example, the headband 18 includes a sleep mode by turning the headband 12 inside out. A switch may be automatically opened as the headband 12 is changed to the sleep mode for disconnecting the pedometer, heart rate monitor 16 and Bluetooth transmitter 22.

Figure 2:
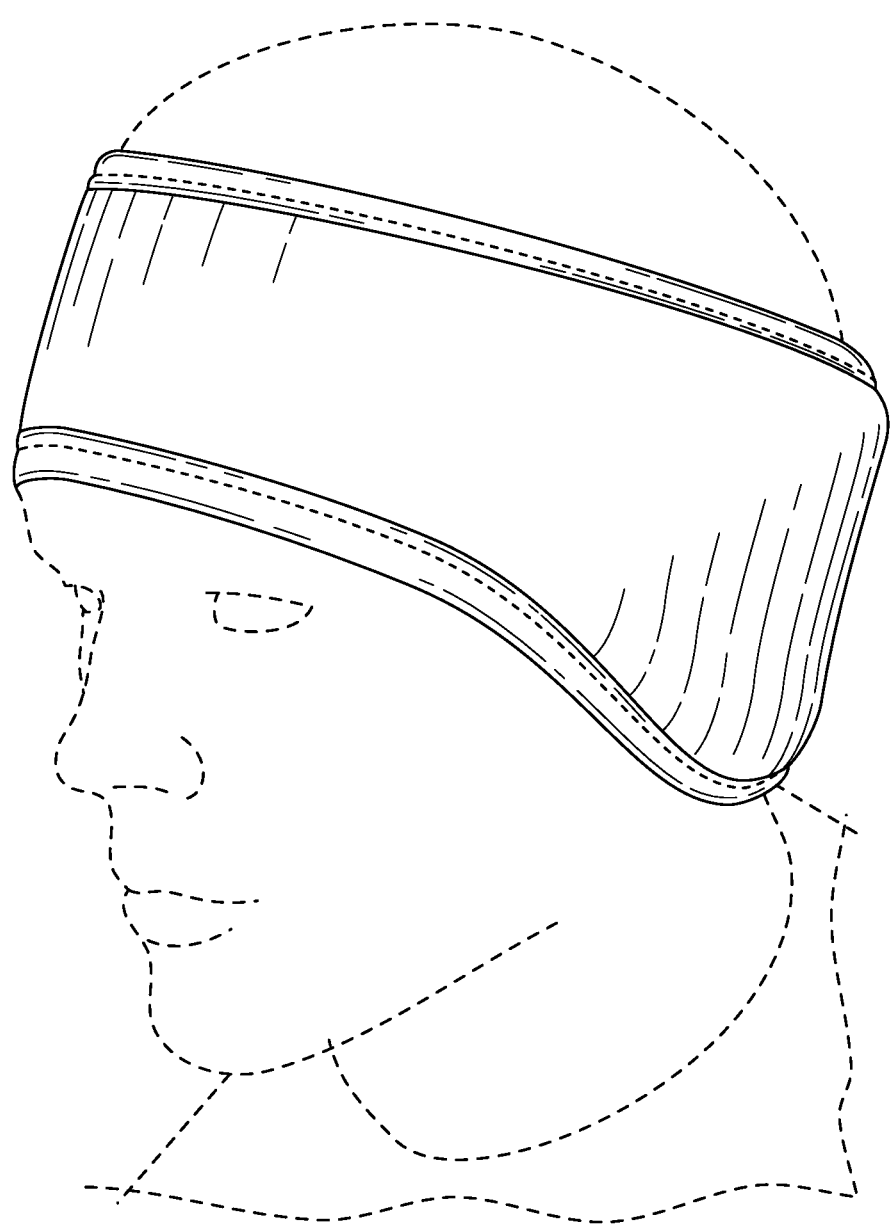
FIG. 2 is a side elevational view of a headband and smartphone in accordance with the invention.
Figure 3:
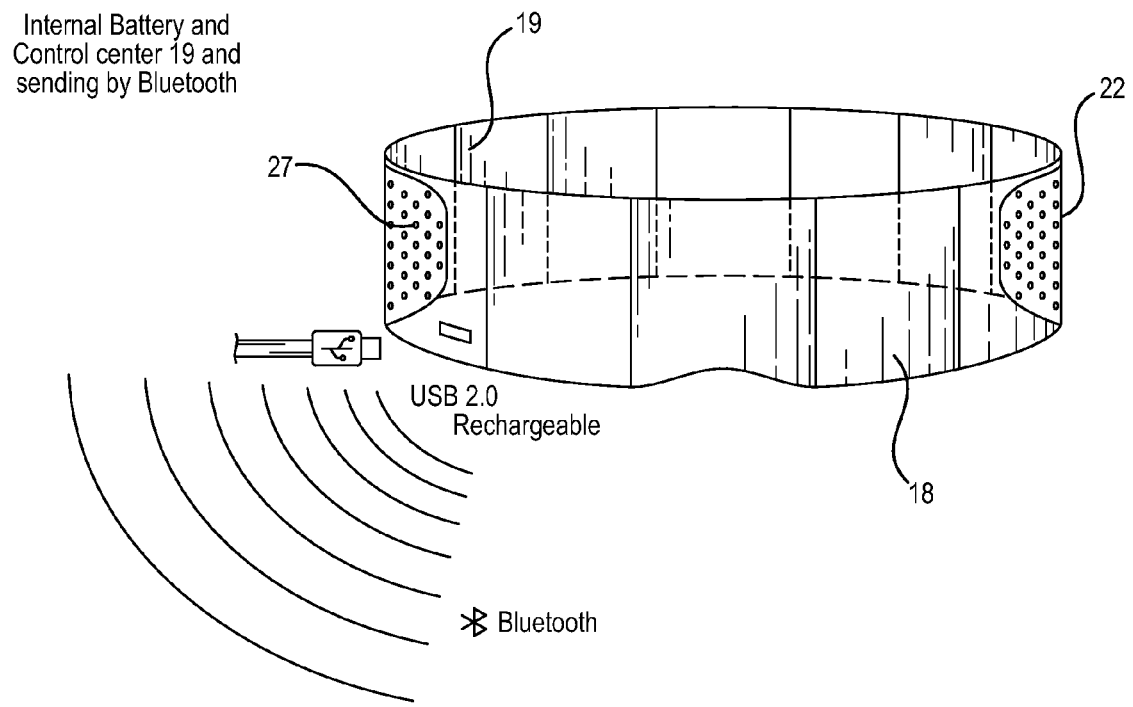
FIG. 3 is a schematic illustration of a system in accordance with one embodiment of the invention.
Figure 3:
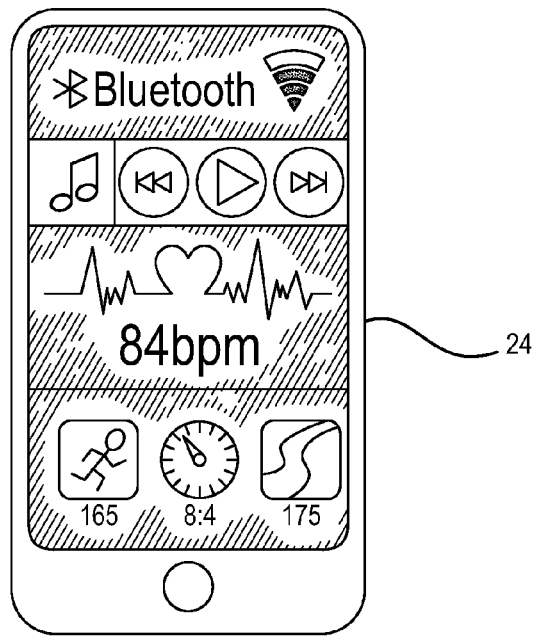

As illustrated in FIG. 2, a headband 12 appears to be a conventional headband of the type worn for protection against cold weather. However, the headband 12 as illustrated in FIG. 3 is operatively connected to a smartphone 24 but for receiving outputs from the pedometer 14, heart rate monitor 16, vibration alarm 18 and Bluetooth connectivity 22. The headband 12 also includes a set of rechargeable batteries 26 that are rechargeable via a USB port 28.

As illustrated in FIG. 3, a smartphone 24 is separated from the headband 12 by a small distance as for example the distance from a person's pocket in their wearing apparel to the headband between a Bluetooth transmitter transmitting from the headband to a smartphone and with a Bluetooth connection. As shown in FIG. 3, the headband includes a vibrator alarm 18 and a set of rechargeable batteries 22 as well as control centers 19. Finally, a USB port 19 may also be provided for recharging the batteries etc.

In addition, the smartphone 24 illustrates the heart rate rhythm such as 84 beats per minute as well as total steps taken or distance traveled and a music selection as well as volume control.

The headband 12 also illustrated in FIG. 2 also includes one or more vibrators 18, a Bluetooth transmitter for sending signals from the pedometer 14 and heart rate monitor 16 as well as the vibrator alarm 18 to the user's smartphone 24. The headband 12 also includes a pair of earphones 22 with one earphone on opposite sides of the generally circular headband. The circular band also has a set of rechargeable batteries 23 as well as a control unit illustrated in an upper portion of a smartphone 24, also illustrated.

Figure 4:
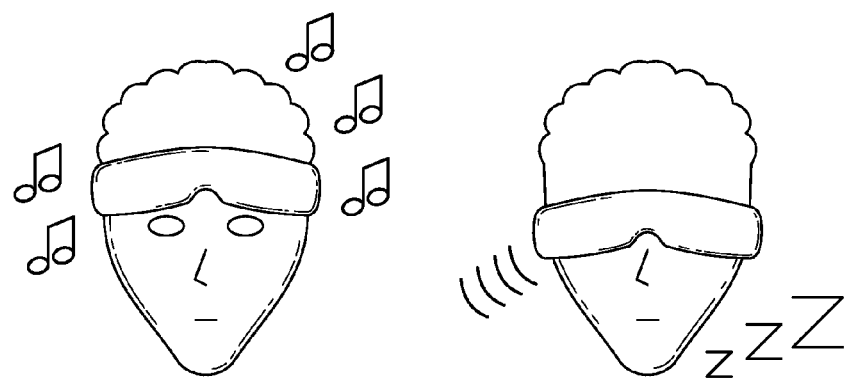
FIG. 4 is a schematic illustration of two embodiments of the invention.

In FIG. 4, a schematic illustration illustrates a sleep mode with the sound of music versus a silent sleep mode separated by an opened switch to eliminate sounds and light in the sleep mode.

While the invention has been described in connection with the preferred embodiment, it should be recognized and understood that changes and modifications may be made therein without departing from the scope of the appended claims.

What is claimed is:

1. A headband monitoring system consisting of:
an elastic/fabric headband adapted for snuggly fitting around an individual's head over the individual's forehead, ears and lower back portion of the individual's head;
a pedometer, a heart rate monitor, a number of sensors and a clock/timer for detecting a number of steps taken and heartbeats in given periods of time and a mini-computer having an input mechanism, data storage, central processing unit for calculating distance traveled in a given period; and
wherein said pedometer and one of said sensors includes a separate pedometer counter portion disposed in said headband and the one of said sensors is adapted to be disposed on the ankle of the individual and wherein the one of said sensors has a wire to connect to said pedometer counter portion; and wherein said heart rate monitor is disposed in said elastic fabric headband and a second of said sensors is adapted to be disposed over the heart of the individual and wherein the second of said sensors has a wire to connect to said heart rate monitor;
an individual's smartphone is separate from the elastic fabric headband and a transmitter disposed in the elastic fabric headband wirelessly connected to the smartphone for displaying heart rate, steps taken and distance traveled on the smartphone; and
a timer and vibrating alarm in the fabric headband for warning an individual that their heart rate has exceeded a predetermined level and that it is time to reduce exertion over a limited period of time before stopping exercise; and
which includes a pair of earphones in the elastic fabric headband and a receiver for a source of music and news deliverable to the earphones from the smartphone; and
which further includes a switch for disconnecting the smartphone from the elastic headband; which includes a sleep mode wherein the headband is adapted to be reversed on an individual's head for relative silence.

* * * * *